US012692468B2

(12) United States Patent
Park et al.

(10) Patent No.: US 12,692,468 B2
(45) Date of Patent: Jul. 28, 2026

(54) BACTERIOSTATIC FILTER SYSTEM FOR ANTIBODY DRUGS PRODUCTION PROCESS, AND METHOD OF OPERATING SAME

(71) Applicant: PRESTIGE BIOLOGICS CO., LTD., Chungcheongbuk-do (KR)

(72) Inventors: Joo Yang Park, Seoul (KR); Ja Won Shin, Sejong (KR); Dae Yang Oh, Seoul (KR)

(73) Assignee: PRESTIGE BIOLOGICS CO., LTD., Cheongju-si Chungcheongbuk-do (KR)

( * ) Notice: Subject to any disclaimer, the term of this patent is extended or adjusted under 35 U.S.C. 154(b) by 933 days.

(21) Appl. No.: 17/910,558

(22) PCT Filed: Mar. 8, 2021

(86) PCT No.: PCT/KR2021/002834
§ 371 (c)(1),
(2) Date: Sep. 9, 2022

(87) PCT Pub. No.: WO2021/194126
PCT Pub. Date: Sep. 30, 2021

(65) Prior Publication Data
US 2023/0151319 A1      May 18, 2023

(30) Foreign Application Priority Data

Mar. 23, 2020     (KR) ........................ 10-2020-0035263

(51) Int. Cl.
*C12M 1/26*        (2006.01)
*C07K 16/00*       (2006.01)
*C12M 1/12*        (2006.01)

(52) U.S. Cl.
CPC ............. *C12M 33/14* (2013.01); *C07K 16/00* (2013.01); *C12M 37/02* (2013.01); *C07K 2317/14* (2013.01)

(58) Field of Classification Search
CPC ..... C12M 33/14; C07K 16/00; C07K 2317/14
(Continued)

(56) References Cited

U.S. PATENT DOCUMENTS

2013/0109086 A1* 5/2013 Kobayashi ............. C12M 47/02
                                                          435/297.1
2015/0140544 A1* 5/2015 Erm ....................... C12M 41/14
                                                          435/3

(Continued)

FOREIGN PATENT DOCUMENTS

DE     102017111133 A1   11/2018
DE     102018107679 A1   10/2019
(Continued)

OTHER PUBLICATIONS

WO2018080178A1 Machine English Translation (Year: 2018).*
(Continued)

*Primary Examiner* — Michael L Hobbs
*Assistant Examiner* — Lenora A Abel
(74) *Attorney, Agent, or Firm* — Dinsmore & Shohl LLP; Yongsok Choi, Esq.

(57)          ABSTRACT

The present invention relates to a bacteriostatic filter system for an antibody drug production process, and to a method of operating same, in which devices are configured and the system is designed so as to enable, through a control unit, the in-lining of a bacteriostatic filter cartridge and in-situ integrity testing of a bacteriostatic filter, wherein according to a result value of the integrity testing, media or buffer are transferred to a storage tank from a preparation tank, or the media or buffer transferred to the storage tank are transferred (Continued)

In-situ wetting, SIP, & integrity tester back to the preparation tank. Accordingly, the present invention can reduce the time required for filter cartridge replacement and integrity testing and implement a system having automated the transferring and backfeeding of media and buffers as well as processing liquids, and can thus reduce the amount of labor needed and shorten the processing time.

13 Claims, 2 Drawing Sheets

(58) Field of Classification Search
USPC ...................................................... 435/291.1
See application file for complete search history.

(56) References Cited

U.S. PATENT DOCUMENTS

| | | | |
|---|---|---|---|
| 2017/0029760 A1 | 2/2017 | Niu | |
| 2017/0349874 A1 | 12/2017 | Jaques et al. | |
| 2019/0322975 A1 | 10/2019 | Nakai | |

FOREIGN PATENT DOCUMENTS

| | | | |
|---|---|---|---|
| JP | 2009-136246 A | 6/2009 | |
| JP | 2011211961 A | * 10/2011 | |
| JP | 2014128780 A | 7/2014 | |
| KR | 10-2002-0026417 A | 4/2002 | |
| KR | 10-2015-0053403 A | 5/2015 | |
| KR | 10-2017-0020307 A | 2/2017 | |
| KR | 10-2018-0047404 A | 5/2018 | |
| KR | 102000200 B1 | 7/2019 | |
| KR | 10-2020-0010441 A | 1/2020 | |
| WO | WO-2018080178 A1 * | 5/2018 | ........... C12N 5/0018 |
| WO | 2019070502 A1 | 4/2019 | |

OTHER PUBLICATIONS

JP2011211961A Machine English Translation (Year: 2011).*
Office Action from corresponding Korean Patent Application No. 10-2020-0035263, dated Aug. 20, 2021.
Yusuf Chisti: "Assure Bioreactor Sterility", Chemical Engineering Progress, American Institute of Chemical Engineers, New York, NY, US, vol. 88, No. 9.
Extended European Search Report for EP 21775218.7 dated May 8, 2024.
International Search Report from corresponding PCT Application No. PCT/KR2021/002834, dated Jun. 23, 2021.

* cited by examiner

In-situ wetting, SIP, & integrity tester

BACTERIOSTATIC FILTER SYSTEM FOR ANTIBODY DRUGS PRODUCTION PROCESS, AND METHOD OF OPERATING SAME

CROSS-REFERENCE TO RELATED APPLICATIONS

This application is a National Phase application of PCT Application No. PCT/KR2021/002834, filed on 8 Mar. 2021, which claims priority to Korean Patent Application No. 10-2020-0035263, filed on 23 Mar. 2020. The entire disclosures of the applications identified in this paragraph are incorporated herein by reference.

TECHNICAL FIELD

The present invention relates to a sterilization filter system for a process of manufacturing an antibody pharmaceutical and an operation method thereof.

BACKGROUND ART

Biopharmaceuticals can be broadly classified into new biologics, improved biopharmaceuticals (biobetters) and biosimilars, and compared with chemically synthesized pharmaceuticals, have fewer side effects and less preclinical data required in research and development, and are easier to predict product efficacy and safety and due to the relatively high probability of clinical success, active development of technology is progressing worldwide.

The process of manufacturing biopharmaceuticals consists of initial candidate material and cell line development, a culture process (upstream processing (USP)), a purification process (downstream processing (DSP)), and a fill and finish process, and particularly, in the case of biosimilar product production, processing optimization in the culture process (USP) and purification process (DSP) is directly related to cost competitiveness, so interest in optimizing the process of manufacturing biosimilars with low cost, high purity and high yield is growing.

In this process, the culture process (USP) corresponds to the process of continuously increasing the number of cells through cell division for approximately 6 weeks from the initial flask stage of less than 1 liter to the final production bioreactor stage of 15,000 L or more, after thawing the cell line, and culture methods that can be used herein include batch culture, fed-batch culture, continuous culture, and perfusion culture and the like.

In addition, the purification process (DSP) is the process of extracting a protein to be used as a pharmaceutical with high purity and high efficiency from the culture in which the cells and cell debris are mixed through the manipulation and use of various types of chromatographs and filters, and during the DSP, column purification, virus removal and ultra/diafiltration are performed through the use of a chromatograph and filters.

Meanwhile, components and systems used in the USP and DSP are divided into stainless steel (SS) and single-use (SU) using disposable bags or tubes in terms of material, and among these, although the SS process system including device components made of SS has advantages of easy implementation on a relatively large scale, low operation cost and easy automation, the initial installation cost is high, it is vulnerable to contamination and prone to the downstream bottleneck phenomenon occurring in the DSP, caused by the implementation of a large-sized bioreactor.

The SU process system, which has recently been introduced, uses disposable bags or tubes with a volume of 0.1 to 2,000 L as device components, and compared to the SS process system, has advantages of relatively low cost for initial installation and being relatively resistant to contamination because a corresponding part can be replaced upon contamination. However, scale-up limitations, continuously-incurring operation costs caused by frequent bag replacement and the input of a lot of labor during equipment replacement are pointed out as disadvantages.

In the field of biopharma today, there are more and more companies serving as contract manufacturing organizations (CMOs) for clinical trials and drugs for commercial use, and furthermore, improvement in one-stop service from cell line development and related process development, scale-up to commercial production is also made.

Meanwhile, in purification and culture processes, a medium, which is a nutrient mixture for cell culture and microbial culture, and a buffer used to stably extract a protein as a liquid buffer and acidity regulator are used, respectively, and the medium and buffer are used after a sterilization process.

The sterilization process is performed by a sterilization filter, EU GMP requires a filter integrity test before and after an aseptic process using a sterilization filter, and when there is a problem with the sterilization filter, contaminants cannot be properly filtered, so it is essential to perform a filter integrity test before/after the use of the sterilization filter.

Meanwhile, conventionally, to test the integrity of a sterilization filter, the integrity of the sterilization filter was checked by removing the entire housing containing the filter, performing a test in a separate location, and then returning the housing to its original position. In this case, depending on the number of transfers of a medium, a buffer and a process liquid, the aforementioned procedure was repeated several times and requires manual operation, so there were problems of excessive input of labor and delayed process time.

DISCLOSURE

Technical Problem

In view of the aforementioned problems, the present invention is directed to providing a sterilization filter system for a process of manufacturing an antibody pharmaceutical, which is able to reduce the time required for filter cartridge exchange and an integrity test and automate the transfer or reverse transfer of a medium and a buffer and the transfer or reverse transfer of a process liquid, leading to decreases in labor and process time, by designing the configuration of components and the system to arrange a sterilization filter cartridge in an in-line manner, perform a sterilization filter integrity test in situ by a control unit, and transfer a medium or buffer from a preparation tank to a storage tank or reversely transfer the medium or buffer transferred to the storage tank to the preparation tank, depending on an integrity test result value, unlike the related art in which the integrity of the sterilization filter was checked by removing the entire housing containing the filter, performing a test in a separate location, and then returning the housing to its original position.

In addition, technological problems to be solved in the present invention are not limited to the above-described technical problems, and other problems which are not described herein will be fully understood by those of ordinary skill in the art from the following descriptions.

Technical Solution

The present specification provides a sterilization filter system for a process of manufacturing an antibody pharmaceutical, which includes: a preparation tank for preparing one selected from a medium and a buffer; a storage tank for storing the medium or buffer received from the preparation tank; a transfer pipeline configured to flow the medium or buffer stream discharged from the preparation tank into the storage tank; a process liquid storage tank for storing a process liquid in the intermediate stage of purification and culture processes; a process liquid transfer pipeline configured to flow the process liquid into the process liquid storage tank; a sterilization filter cartridge disposed on one or more selected from the transfer pipeline and the process liquid transfer pipeline; and a control unit, wherein the sterilization filter cartridge includes, for a washing and filter test process including one or more selected from filter sterilization, filter wetting, flushing, filter integrity test, air ballasting and barrier integrity testing, a first pipeline entering the sterilization filter cartridge and a second pipeline exiting the sterilization filter cartridge.

In the present specification, the sterilization filter system for a process of manufacturing an antibody pharmaceutical further includes an integrity tester on the first pipeline entering the sterilization filter cartridge.

In the present specification, in the sterilization filter system for a process of manufacturing an antibody pharmaceutical, the control unit automatically transfers a medium or buffer from the preparation tank to the storage tank or reversely transfers the medium or buffer transferred to the storage tank to the preparation tank, depending on a filter integrity test result value.

In addition, in the present specification, the control unit automatically transfers the process liquid to the process liquid storage tank or reversely transfers the process liquid transferred to the process liquid storage tank along the process liquid transfer pipeline, depending on a filter integrity test result value.

In addition, in the present specification, the sterilization filter system is applied to transfer one or more of a medium, a buffer and a process liquid in the process of manufacturing one or more antibody pharmaceuticals selected from the group consisting of abagovomab, abciximab, adalimumab, adecatumumab, alemtuzumab, altumomab, altumomab pentetate, anatumomab, anatumomab mafenatox, arcitumomab, atlizumab, basiliximab, bectumomab, bectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, ustekinumab, visilizumab, votumumab, zalutumumab, brodalumab, anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, adornase alfa, Rebif, becaplermin, alteplase, laronidase, alefacept, aflibercept, raxibacumab, darbepoetin alfa, becaplermin concentrate, interferon beta-1b, botulinum toxin type A, rasburicase, asparaginase, epoetin alfa, etanercept, agalsidase beta, interferon alfacon-1, interferon alfa-2a, anakinra, botulinum toxin type B, pegfilgrastim, oprelvekin, filgrastim, denileukin diftitox, peginterferon alfa-2a, aldesleukin, dornase alfa, interferon beta-1a, becaplermin, reteplase, interferon alfa-2, tenecteplase, drotrecogin alfa, rilonacept, romiplostim, methoxypolyethylene glycol-epoetin beta, a C1 esterase inhibitor, idursulfase, alglucosidase alfa, abatacept, galsulfase, palifermin and interferon gamma-1b.

In addition, the present specification provides a method of operating the sterilization filter system, which includes sequentially performing filter sterilization, filter wetting, flushing, a first filter integrity test, air ballasting and a barrier integrity test, transferring one or more selected from a medium, a buffer and a process liquid using an automatic valve, and following the completion of the transfer of one or more selected from a medium, a buffer and a process liquid, sequentially performing filter wetting, flushing, a second filter integrity test using an automatic valve, along the first pipeline, the filter cartridge and the second pipeline.

In addition, in the present specification, the filter integrity test includes one or more tests selected from a forward flow integrity test (FFIT), a bubble point test (BPT), and a pressure hold test (PHT).

In addition, in the present specification, the control unit automatically transfers a medium or a buffer from the preparation tank to the storage tank when the first filter integrity test result value satisfies a preset reference value, and sends a sterilization filter replacement alarm when the first filter integrity test result value does not satisfy the preset reference value.

In addition, in the present specification, the control unit continues the washing and filter test process when the second filter integrity test result value satisfies a preset reference value, and reversely transfers the medium or buffer transferred to the storage tank to the preparation tank when the second filter integrity test result value does not satisfy the preset reference value.

In addition, in the present specification, the control unit automatically transfers a process liquid to the process liquid storage tank along the process liquid transfer pipeline when the first filter integrity test result value satisfies a preset reference value, and sends a sterilization filter replacement alarm when the first filter integrity test result value does not satisfy the preset reference value.

In addition, in the present specification, the control unit continues the washing and filter test process when the second filter integrity test result value satisfies a preset reference value, and reversely transfers the process liquid transferred to the process liquid storage tank along the process liquid transfer pipeline when the second filter integrity test result value does not satisfy the preset reference value.

Advantageous Effects

A sterilization filter system and operation method according to the present invention can reduce the time for filter cartridge exchange and integrity testing by designing the configuration of components and the system to arrange a sterilization filter cartridge in an in-line manner, perform a sterilization filter integrity test in situ by a control unit, and transfer a medium or buffer from a preparation tank to a storage tank or reversely transfer the medium or buffer transferred to the storage tank to the preparation tank, depending on an integrity test result value, unlike the related art in which the integrity of the sterilization filter was checked by removing the entire housing containing the filter, performing a test in a separate location, and then returning the housing to its original position.

In addition, the sterilization filter system and operation method according to the present invention can reduce labor and process time by implementing a system that automates the transfer and reverse transfer of a medium and a buffer using a control unit, and further the transfer and reverse transfer of a process liquid.

Accordingly, in the manufacture of antibody pharmaceuticals, when the sterilization filter system is adopted, process costs and efficiency can be improved, and a smart factory can be more effectively implemented.

MODES OF THE INVENTION

Figure 1:
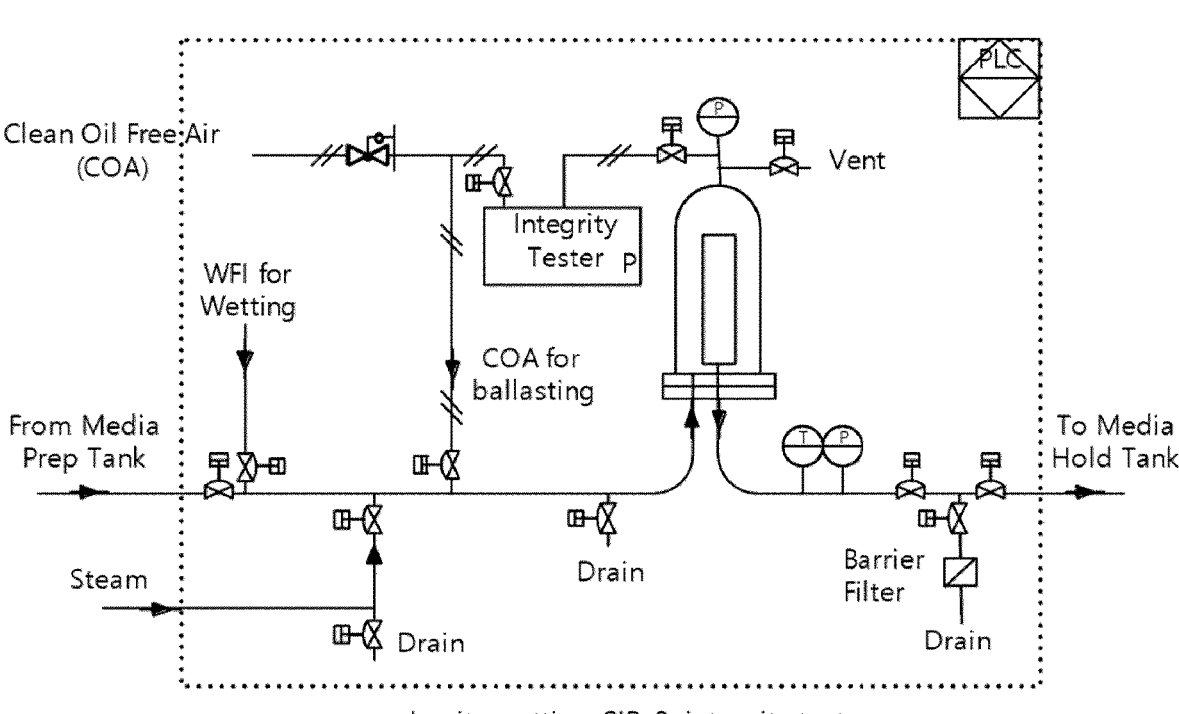
FIG. 1 schematically shows a sterilization filter system for a process of manufacturing an antibody pharmaceutical, implemented according to one embodiment of the present invention.

The terms used in the specification are used only to describe specific examples, not to limit the present invention. Singular expressions include plural expressions unless clearly indicated otherwise in the context. It should be understood that the term "comprise," "include," or "have" used herein is for indicating the presence of implemented characteristics, numbers, steps, elements or a combination thereof, and does not preclude the possibility of the presence or addition of one or more other characteristics, numbers, steps, elements or a combination thereof.

In addition, in the present invention, when a layer or element is referred to as being formed "on" or "over" each layer or element, it is meant that each layer or element is formed directly on each layer or element, or another layer or element is formed on each layer, or that another layer or element may additionally be formed between layers, on an object, or a substrate.

The present invention may have various modifications and various examples, and thus specific examples are illustrated in the drawings and described in detail in the detailed description. However, it should be understood that the present invention is not limited to specific embodiments, and includes all modifications, equivalents or alternatives within the spirit and technical scope of the present invention.

In addition, in the present invention, the term "unit" used throughout the specification and claims may mean a software or hardware component, and the "unit" performs a certain role. However, the "unit" is not limited to software or hardware. The "unit" may be configured to be present in an addressable storage medium or to regenerate one or more processors. Therefore, in one example, the "unit" includes components such as software components, object-oriented software components, class components and task components, processors, functions, properties, procedures, subroutines, segments of program code, drivers, firmware, microcode, circuit, data, database, data structures, tables, arrays, and variables. The functions provided in the components and "units" may be combined into a smaller number of components and "units", or further separated into additional components and "units."

According to one embodiment of the present invention, the "unit" may be implemented as a processor and a memory. The term "processor" should be construed broadly to include a general-purpose processor, a central processing unit (CPU), a microprocessor, a digital signal processor (DSP), a controller, a microcontroller, and a state machine. In some circumstances, the "processor" may refer to an application-specific integrated circuit (ASIC), a programmable logic device (PLD), or a field programmable gate array (FPGA). The term "processor" may also refer to a combination of processing devices, for example, a combination of DSP and a microprocessor, a combination of a plurality of microprocessors, a combination of one or more microprocessors combined with a DSP core, or a combination of random components.

The term "memory" should be construed broadly to include any electron component that can store electron information. The term "memory" may also refer to various types of processor-readable media such as a random access memory (RAM), a read-only memory (ROM), a non-volatile random access memory (NVRAM), a programmable read-only memory (PROM), an erase-programmable read-only memory (EPROM), an electrically erasable PROM (EE-PROM), a flash memory, magnetic or optical data storage devices, and registers. A memory is said to be in electronic communication with the processor if the processor is capable of reading information from and/or writing information to the memory. The memory integrated in the processor is in electronic communication with the processor.

Hereinafter, a sterilization filter system for a process of manufacturing an antibody pharmaceutical and an operating method thereof according to exemplary embodiments of the present invention will be described in further detail.

Sterilization Filter System for Process of Manufacturing Antibody Pharmaceutical A sterilization filter system for a process for manufacturing an antibody pharmaceutical according to one embodiment of the present invention includes a preparation tank for preparing one selected from a medium and a buffer; a storage tank for storing the medium or buffer received from the preparation tank; a transfer pipeline configured to flow the medium or buffer stream discharged from the preparation tank into the storage tank; a process liquid storage tank for storing a process liquid in the intermediate stage of purification and culture processes; a process liquid transfer pipeline configured to flow the process liquid into the process liquid storage tank; a sterilization filter cartridge disposed on one or more selected from the transfer pipeline and the process liquid transfer pipeline; and a control unit, wherein the sterilization filter cartridge may include, for a washing and filter test process including one or more selected from filter sterilization, filter wetting, flushing, filter integrity test, air ballasting and barrier integrity testing, a first pipeline entering the sterilization filter cartridge and a second pipeline exiting the sterilization filter cartridge (see FIG. 1).

Meanwhile, in one embodiment of the present invention, a medium preparation tank of the preparation tank may be connected with a medium storage tank, and a buffer preparation tank of the preparation tank, and the buffer preparation tank of the preparation tank may be connected with a buffer storage tank.

In further detail, the process of manufacturing an antibody pharmaceutical consists of initial candidate material and cell line development, a culture process (USP), a purification process (DSP), and a fill and finish process.

In this process, the culture process (USP) corresponds to the process of continuously increasing the number of cells through cell division for approximately 6 weeks from the initial flask stage of less than 1 liter to the final production bioreactor stage of 15,000 L or more, after thawing the cell line.

The cultivation unit according to one embodiment of the present invention is a set of components for the culture process, which may include a medium preparation tank for preparing a medium in advance, a medium storage tank for receiving the media from the medium preparation tank and storing the medium, a feed line through which a feed stream including thawed cells and a culture medium is introduced into a bioreactor, one or more bioreactors including a stirring system, which receive the thawed cells and the medium from the feed stream and increase the number of cells through cell division, and a discharge line which discharges the medium containing the cells cultured in the bioreactor as an effluent stream.

In addition, the purification unit according to one embodiment of the present invention is a set of components for the purification process (DSP), which may include a buffer preparation tank for preparing a buffer in advance, a buffer storage tank for receiving the buffer from the buffer preparation tank and storing the buffer, a chromatograph for removing impurities mixed in the medium using the medium received from the cultivation unit and the buffer transferred from the buffer storage tank to increase the purity of a target protein, and one or more filtration systems which are disposed before or after the chromatograph to perform buffer exchange and concentration.

In addition, in an intermediate procedure of the culture and purification processes, a process liquid storage tank for storing a process liquid and a process liquid transfer pipeline configured to introduce the process liquid into the process liquid storage tank may be further included.

Meanwhile, the preparation tank and storage tank for one selected from a medium and a buffer, and the medium, buffer or process liquid transfer pipeline may be formed of one or more materials selected from an SS material and an SU disposable bag, or may be hybrid systems formed of a mixture thereof.

Meanwhile, in purification and culture processes, a medium, which is a nutrient mixture for cell culture and microbial culture, and a buffer used to stably extract a protein as a liquid buffer and acidity regulator are used, respectively, and the medium and buffer are used after a sterilization process.

The sterilization process is performed by a sterilization filter, EU GMP requires a filter integrity test before and after an aseptic process using a sterilization filter, and when there is a problem with the sterilization filter, contaminants cannot be properly filtered, so it is essential to perform a filter integrity test before/after the use of the sterilization filter.

Meanwhile, conventionally, to test the integrity of a sterilization filter, the integrity of the sterilization filter was checked by removing the entire housing containing the filter, performing a test in a separate location, and then returning the housing to its original position. In this case, depending on the number of transfers of a medium, a buffer and a process liquid, the aforementioned procedure was repeated several times and requires manual operation, so there were problems of excessive input of labor and delayed process time.

The present inventors confirmed that, unlike the related art in which the integrity of the sterilization filter was checked by removing the entire housing containing the filter, performing a test in a separate location, and then returning the housing to its original position, when the configuration of components and a system are designed to arrange a sterilization filter cartridge in an in-line manner, perform a sterilization filter integrity test in situ by a control unit, and transfer a medium or buffer from a preparation tank to a storage tank or reversely transfer the medium or buffer transferred to the storage tank to the preparation tank, depending on an integrity test result value, the system that can reduce the time required for filter cartridge exchange and an integrity test and automate the transfer or reverse transfer of a medium and a buffer and the transfer or reverse transfer of a process liquid, leading to decreases in labor and process time, and thus completed the present invention.

Specifically, according to one embodiment of the present invention, the sterilization filter cartridge including a sterilization filter may include a first pipeline which is disposed on one or more lines selected from the medium or buffer feed pipeline and the process liquid transfer pipeline and introduced into the sterilization filter cartridge and a second pipeline exiting the sterilization filter cartridge for a washing and filter test process including one or more selected from filter sterilization, filter wetting, flushing, filter integrity test, air ballasting and barrier integrity testing.

In the present invention, as described above, by installing the sterilization filter cartridge on the feed pipeline and/or the process liquid transfer pipeline in an in-line manner, labor for the attachment/detachment and movement of the filter cartridge, and process time are reduced.

In addition, an integrity tester may be provided on the first pipeline entering the sterilization filter cartridge (see FIG. 1).

The filter integrity tester is a component for performing physical, non-destructive testing for investigating whether there are defects in a filter membrane in order to prevent the leakage of contaminants due to the damage or defect in the filter or the failure of the original function of the filter, and one or more tests selected from a forward flow integrity test (FFIT), a bubble point test (BPT) and a pressure hold test (PHT) may be performed using the aforementioned component.

Specifically, the FFIT test is also referred to a diffusion test, which is based on a principle that compressed air or nitrogen gas passes through a liquid filling the pores of the filter by diffusion when pressure is applied with a differential pressure of a bubble point or less. Meanwhile, the BPT test is a test based on a principle that a liquid is contained in the pores of a filter by surface tension and capillary force, and the BPT test measures the minimum pressure required to push a liquid out of the pores of the membrane filter by exceeding the surface tension and the capillary force. Meanwhile, the PHT test is also referred to a pressure decay or pressure drop test, which is a method of monitoring a pressure change at the upper part of a filter due to diffusion or leakage of a gas passing through the filter, and uses a very precise pressure gauge.

Meanwhile, different from the feed pipeline and/or the process liquid transfer pipeline, the first pipeline entering the sterilization filter cartridge and the second pipeline exiting the sterilization filter cartridge are configured to perform a process such as wetting or air ballasting, and clean and oil-free air (COA) may be introduced into the sterilization filter cartridge or discharged out of the cartridge along the first or second pipeline, respectively.

Meanwhile, the in-line sterilization filter cartridge according to one embodiment of the present invention may undergo a washing and filter test processes including one or more selected from filter sterilization, filter wetting, flushing, filter integrity test, air ballasting and barrier integrity testing, and the specific order of processes performed and which processes are specifically included may be differently selected before and after transfer of one selected from a medium, a buffer and a process liquid.

In one example, referring to FIG. 1, in the culture process, filter sterilization, filter wetting, flushing, a first filter integrity test, air ballasting and a barrier integrity test may be sequentially performed using an automatic valve before medium transfer, and filter wetting, flushing and a second filter integrity test may be sequentially performed using an automatic valve after medium transfer, which is possible to design and change appropriately.

Meanwhile, the transfer of a medium, a buffer and a process liquid and the washing and filter test may be controlled by a control unit, and the control unit may be a component configured to automatically transfer a medium or buffer from the preparation tank to a storage tank or reverse-transfer the medium or buffer transferred to the storage tank to a preparation tank by comparing a filter integrity test result value with the preset reference value (reference).

In addition, the control unit may be a component configured to automatically transfer the process liquid to the process liquid storage tank or reverse-transfer the process liquid transferred to the process liquid storage tank along the process liquid transfer pipeline by comparing the filter integrity test result value with the preset reference value (reference).

Specifically, the control unit may include one or more components selected from a processor and a memory, and the process may execute instructions stored in the memory. Meanwhile, the processor may include, for example, a central processing unit (CPU), a graphics processing device (GPU) or both, and in one example, may be of a type in which the process operation is automated (adjusted and controlled) by the processor and the memory in the control unit. In one example, the control unit according to one embodiment of the present invention may be a programmable logic controller (PLC).

Meanwhile, the sterilization filter system according to one embodiment of the present invention may be applied to transfer one or more of a medium, a buffer and a process liquid in the process of manufacturing one or more antibody pharmaceuticals selected from the group consisting of abagovomab, abciximab, adalimumab, adecatumumab, alemtuzumab, altumomab, altumomab pentetate, anatumomab, anatumomab mafenatox, arcitumomab, atlizumab, basiliximab, bectumomab, bectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, ustekinumab, visilizumab, votumumab, zalutumumab, brodalumab, anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, adornase alfa, Rebif, becaplermin, alteplase, laronidase, alefacept, aflibercept, raxibacumab, darbepoetin alfa, becaplermin concentrate, interferon beta-1b, botulinum toxin type A, rasburicase, asparaginase, epoetin alfa, etanercept, agalsidase beta, interferon alfacon-1, interferon alfa-2a, anakinra, botulinum toxin type B, pegfilgrastim, oprelvekin, filgrastim, denileukin diftitox, peginterferon alfa-2a, aldesleukin, dornase alfa, interferon beta-1a, becaplermin, reteplase, interferon alfa-2, tenecteplase, drotrecogin alfa, rilonacept, romiplostim, methoxypolyethylene glycol-epoetin beta, a C1 esterase inhibitor, idursulfase, alglucosidase alfa, abatacept, galsulfase, palifermin and interferon gamma-1b, and may be variously applied throughout a process of manufacturing antibody pharmaceuticals, such as biopharmaceuticals, improved biopharmaceuticals (biobetters) and biosimilars.

Figure 2:
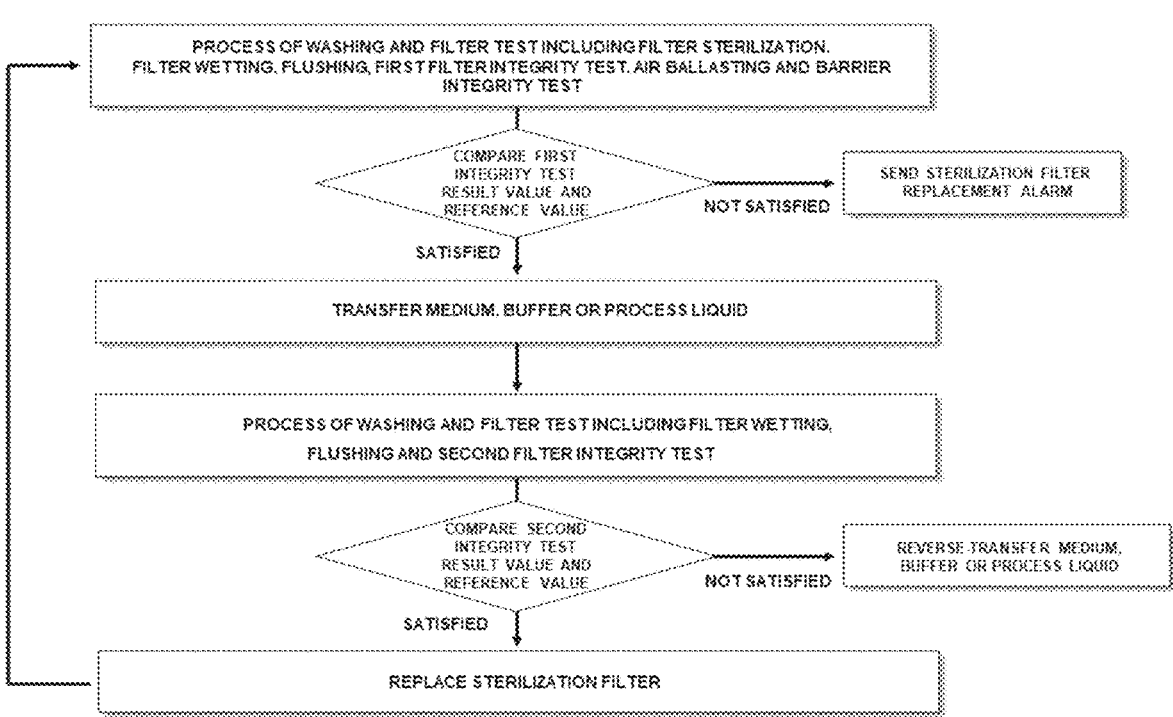
FIG. 2 shows a flowchart of a method of operating a sterilization filter system for a process of manufacturing an antibody pharmaceutical according to one embodiment of the present invention.

Method of Operating Sterilization Filter System for Process of Manufacturing Antibody Pharmaceutical Meanwhile, the method of operating a sterilization filter system according to one embodiment of the present invention may include sequentially performing filter sterilization, filter wetting, flushing, a first filter integrity test, air ballasting and a barrier integrity test, transferring one or more selected from a medium, a buffer and a process liquid using an automatic valve, and following the completion of the transfer of one or more selected from a medium, a buffer and a process liquid, sequentially performing filter wetting, flushing, a second filter integrity test using an automatic valve, along the first pipeline, the filter cartridge and the second pipeline (see FIG. 2).

Meanwhile, it should be understood that the terms "first" and "second" used throughout the specification and claims of the present invention are intended to arbitrarily determine an order.

Meanwhile, the filter integrity test may include one or more tests selected from a forward flow integrity test (FFIT), a bubble point test (BPT) and a pressure hold test (PHT), and a specific test method is as described above.

Meanwhile, in the method of operating a sterilization filter system according to one embodiment of the present invention, the control unit may automatically transfer a medium or a buffer from the preparation tank to the storage tank when the first filter integrity test result value satisfies a preset reference value, and send a sterilization filter replacement alarm when the first filter integrity test result value does not satisfy the preset reference value.

In addition, in the method of operating a sterilization filter system according to another embodiment of the present invention, the control unit may continuously perform the washing and filter test process when the second filter integrity test result value satisfies a preset reference value, and reversely transfer the medium or buffer transferred to the storage tank to the preparation tank when the second filter integrity test result value does not satisfy the preset reference value.

In addition, in the method of operating a sterilization filter system according to still another embodiment of the present invention, the control unit may automatically transfer a process liquid to the process liquid storage tank along the process liquid transfer pipeline when the first filter integrity test result value satisfies a preset reference value, and send a sterilization filter replacement alarm when the first filter integrity test result value does not satisfy the preset reference value.

11

12

In addition, in the method of operating a sterilization filter system according to yet another embodiment of the present invention, the control unit may continuously perform the washing and filter test process when the second filter integrity test result value satisfies a preset reference value, and reversely transfer the process liquid transferred to the process liquid storage tank along the process liquid transfer pipeline when the second filter integrity test result value does not satisfy the preset reference value.

In one example, when the control unit according to one embodiment of the present invention is a programmable logic controller (PLC), by using an in-line sterilization filter cartridge, a built-in integrity tester and an automatic valve, the required process is programmed and logicized in series, thereby performing an automated filter integrity test with the push of a button.

In one example, after the installation of a disposable sterilization filter cartridge in an SS housing before medium transfer, filter sterilization, filter wetting, flushing, a first filter integrity test using process COA, air ballasting and a barrier integrity test are sequentially performed in an in-line manner. Here, the control unit automatically transfers a medium from the preparation tank to the storage tank when the first filter integrity test result value satisfies a preset reference value, and sends a sterilization filter replacement alarm when the first filter integrity test result value does not satisfy the preset reference value.

After the completion of the medium transfer, the control unit sequentially performs filter wetting, flushing and a second filter integrity test using an automatic valve, and here, when the second filter integrity test result value satisfies the preset reference value, after replacing the filter cartridge for a subsequent process, the aforementioned washing and filter test process proceeds to a subsequent step to restart, and when the second filter integrity test result value does not satisfy the preset reference value, the medium transferred to the storage tank is reversely transferred to the preparation tank.

As described above, the control unit automates the transfer or reverse-transfer of a medium, a buffer and a process liquid by comparing the filter integrity test result value with the preset reference value, so an in-situ process can be performed directly on site without moving equipment for testing.

As described above, according to the sterilization filter system and operation method according to the present invention, the time for filter cartridge replacement and integrity testing may be reduced by designing the configuration of components and a system to arrange a sterilization filter cartridge in an in-line manner, perform a sterilization filter integrity test in situ by a control unit, and transfer a medium or buffer from a preparation tank to a storage tank or reversely transfer the medium or buffer transferred to the storage tank to the preparation tank, depending on an integrity test result value.

In addition, the sterilization filter system and operation method according to the present invention may implement a system automating the transfer and reverse-transfer of a medium and a buffer, and further the transfer and reverse-transfer of a process liquid using the control unit, thereby reducing labor and the process time.

Accordingly, in the manufacture of antibody pharmaceuticals, when the sterilization filter system is adopted, process costs and efficiency can be improved, and a smart factory can be more effectively implemented.

In the above, the present invention has been described with reference to exemplary embodiments, but the present invention is not limited to the described embodiments, and it is obvious to those skilled in the art or those of ordinary skill in the art that the present invention can be variously modified and changed without departing the spirit and scope of the present invention. Accordingly, such modifications or variations should not be individually understood from the technical spirit or point of view of the present invention, and the modified embodiments should belong to the claims of the present invention.

What is claimed is:

1. A sterilization filter system for a process of manufacturing an antibody pharmaceutical, comprising:
   a preparation tank for preparing one selected from a medium and a buffer;
   a storage tank for storing the medium or buffer received from the preparation tank;
   a transfer pipeline configured to flow the medium or buffer stream discharged from the preparation tank into the storage tank;
   a process liquid storage tank for storing a process liquid in the intermediate stage of purification and culture processes;
   a process liquid transfer pipeline configured to flow the process liquid into the process liquid storage tank;
   a sterilization filter cartridge disposed on one or more selected from the transfer pipeline and the process liquid transfer pipeline; and
   a control unit,
   wherein the sterilization filter cartridge comprises, for a washing and filter test process including one or more selected from filter sterilization, filter wetting, flushing, filter integrity test, air ballasting and barrier integrity testing, a first pipeline entering the sterilization filter cartridge, and a second pipeline exiting the sterilization filter cartridge,
   wherein the first pipeline and the second pipeline are separate from the transfer pipeline and the process liquid transfer pipeline,
   wherein the first pipeline and the second pipeline are configured to supply and discharge a test fluid for performing the washing and filter test process, and
   wherein the washing and filter test process is performed while the sterilization filter cartridge remains disposed on the transfer pipeline or the process liquid transfer pipeline.

2. The system of claim 1, wherein an integrity tester is provided on the first pipeline entering the sterilization filter cartridge.

3. The system of claim 1, wherein the control unit automatically transfers a medium or buffer from the preparation tank to the storage tank or reversely transfers the medium or buffer transferred to the storage tank to the preparation tank, depending on a filter integrity test result value.

4. The system of claim 1, wherein the control unit automatically transfers the process liquid to the process liquid storage tank or reversely transfers the process liquid transferred to the process liquid storage tank along the process liquid transfer pipeline, depending on a filter integrity test result value.

5. The system of claim 1, wherein the sterilization filter system is applied to transfer one or more of a medium, a buffer and a process liquid in the process of manufacturing one or more antibody pharmaceuticals selected from the group consisting of abagovomab, abciximab, adalimumab, adecatumumab, alemtuzumab, altumomab, altumomab pentetate, anatumomab, anatumomab mafenatox, arcitumomab, atlizumab, basiliximab, bectumomab, bectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, ustekinumab, visilizumab, votumumab, zalutumumab, brodalumab, anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, adornase alfa, Rebif, becaplermin, alteplase, laronidase, alefacept, aflibercept, raxibacumab, darbepoetin alfa, becaplermin concentrate, interferon beta-1b, botulinum toxin type A, rasburicase, asparaginase, epoetin alfa, etanercept, agalsidase beta, interferon alfacon-1, interferon alfa-2a, anakinra, botulinum toxin type B, pegfilgrastim, oprelvekin, filgrastim, denileukin diftitox, peginterferon alfa-2a, aldesleukin, dornase alfa, interferon beta-1a, becaplermin, reteplase, interferon alfa-2, tenecteplase, drotrecogin alfa, rilonacept, romiplostim, methoxypolyethylene glycol-epoetin beta, a C1 esterase inhibitor, idursulfase, alglucosidase alfa, abatacept, galsulfase, palifermin and interferon gamma-1b.

6. A method of operating the sterilization filter system of claim 1, comprising:

sequentially performing filter sterilization, filter wetting, flushing, a first filter integrity test, air ballasting and a barrier integrity test, transferring one or more selected from a medium, a buffer and a process liquid using an automatic valve, and following the completion of the transfer of one or more selected from a medium, a buffer and a process liquid, sequentially performing filter wetting, flushing, a second filter integrity test, using an automatic valve, along the first pipeline, filter cartridge and second pipeline.

7. The method of claim 6, wherein the filter integrity test comprises one or more tests selected from a forward flow integrity test (FFIT), a bubble point test (BPT), and a pressure hold test (PHT).

8. The method of claim 6, wherein the control unit automatically transfers a medium or a buffer from the preparation tank to the storage tank when the first filter integrity test result value satisfies a preset reference value, and sends a sterilization filter replacement alarm when the first filter integrity test result value does not satisfy the preset reference value.

9. The method of claim 6, wherein the control unit continues the washing and filter test process when the second filter integrity test result value satisfies a preset reference value, and reversely transfers the medium or buffer transferred to the storage tank to the preparation tank when the second filter integrity test result value does not satisfy the preset reference value.

10. The method of claim 6, wherein the control unit automatically transfers a process liquid to the process liquid storage tank along the process liquid transfer pipeline when the first filter integrity test result value satisfies a preset reference value, and sends a sterilization filter replacement alarm when the first filter integrity test result value does not satisfy the preset reference value.

11. The method of claim 6, wherein the control unit continues the washing and filter test process when the second filter integrity test result value satisfies a preset reference value, and reversely transfers the process liquid transferred to the process liquid storage tank along the process liquid transfer pipeline when the second filter integrity test result value does not satisfy the preset reference value.

12. The system of claim 1,
wherein the test fluid flows through the sterilization filter cartridge from the first pipeline to the second pipeline independently of a flow of the medium, buffer, or process liquid through the transfer pipeline or the process liquid transfer pipeline.

13. The system of claim 1,
wherein the test fluid is not delivered to the storage tank or the process liquid storage tank.

* * * * *